United States Patent [19]

Longobardi et al.

[11] 4,120,857

[45] Oct. 17, 1978

[54] DERIVATIVES OF 1,2,3,3-TETRAMETHYL-2-AZABICYCLO[2.2.2]OCTAN-5-ENDO-OL

[76] Inventors: Mario Longobardi, Via S. Martino 49/4, 16131 Genova; Pietro Schenone, Via Zara 25-1, 16145 Genova; Francesco Bondavalli, Via Genova 6F/13, 17100 Savona, all of Italy

[21] Appl. No.: 791,096

[22] Filed: Apr. 26, 1977

[51] Int. Cl.$^2$ ............................................. C07D 221/24
[52] U.S. Cl. .................................................. 260/293.54
[58] Field of Search ..................................... 260/293.54

[56] References Cited

U.S. PATENT DOCUMENTS

| | | | |
|---|---|---|---|
| 3,808,263 | 4/1974 | Yoneda et al. | 260/293.54 |
| 3,875,169 | 4/1975 | Ramey et al. | 260/293.54 |

*Primary Examiner*—Henry R. Jiles
*Assistant Examiner*—Richard A. Schwartz
*Attorney, Agent, or Firm*—David M. Morse

[57] ABSTRACT

Novel ester and ether derivatives of 1,2,3,3-tetramethyl-2-azabicyclo[2.2.2]octan-5-endo-ol have been prepared and found to possess antiarrhythmic or antihypertensive activity. An example of such a derivative possessing excellent antiarrhythmic activity is 5-endo-(3-benzoylaminopropyloxy)-1,2,3,3-tetramethyl-2-azabicyclo[2.2.2]octane.

10 Claims, No Drawings

– 1 –

DERIVATIVES OF 1,2,3,3-TETRAMETHYL-2-AZABICYCLO[2.2.2]OCTAN-5-ENDO-OL

BACKGROUND OF THE INVENTION

1. Field of the Invention

This invention relates to novel derivatives of 1,2,3,3-tetramethyl-2-azabicyclo[2.2.2]octan-5-endo-ol possessing anti-arrhythmic or antihypertensive activity.

2. Description of the Prior Art

Antiarrhythmic activity has been found in a wide variety of synthetic amines, amino esters and amino amides, e.g. procaine, procainamide and lidocaine. Among such compounds are glycinamides derived from bridged bicyclic nuclei such as bicyclo[2.2.1]heptane and bicyclo[2.2.2]octane [see *J. Med. Pharm. Chem.* 4:183 (1961)] as well as from 6-amino-1,3,3-trimethyl-2-oxabicyclo[2.2.2]octane [see *Il Farmaco Ed. Sci.* 18:828 (1963); ibid 19:556 (1964)]. In these basic amides the antiarrhythmic activity has been ascribed to the resistance to hydrolysis of the amido group caused by the shielding effect of the highly hindered three-dimensional bicyclic ring.

Various derivatives of 2-azabicyclo[2.2.2]octane have been prepared and shown to possess interesting pharmacological properties such as local anesthetic, cholinergic, analgesic and ganglion blocking activities. Among such derivatives are those disclosed in *J. Het. Chem.* 11:311–315 (1974), *J. Pharm. Sci.* 63:1559–1562 (1974), *Chem. Abstr.* 70:96653j (1969), *J. Med. Chem.* 15:374–378 (1972), *Chem. Abstr.* 70:28834U (1969), *J. Med. Chem.* 16:853–856 (1973) and *J. Pharm. Sci.* 59:98–100 (1970).

The compound 1,3,3-trimethyl-2-azabicyclo[2.2.2]octan-5-endo-ol having the formula

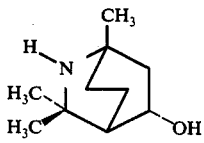

is disclosed without mention of any pharmacological activity in *Tetrahedron* 28:741 (1972). The above-mentioned alcohol is the starting material for preparation of the compounds of the present invention.

THE INVENTION

This invention comprises the novel compounds having the general formula

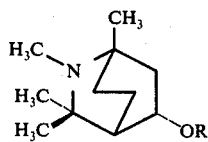

wherein R is —$COR_1$ in which $R_1$ is (lower)alkyl, cyclo(lower)-alkyl, phenyl, p-aminophenyl, 3,4,5-trimethoxyphenyl or diphenylmethyl, —$CONHR_2$ in which $R_2$ is phenyl, or —$(CH_2)_3NHCOR_3$ in which $R_3$ is phenyl or diphenylmethyl; and the pharmaceutically acceptable acid addition salts thereof.

The term "pharmaceutically acceptable acid addition salt" is meant to include all those organic and inorganic acid salts of the compounds of formula I, which salts are commonly used as substantially nontoxic salts of medicinal agents containing amine functions. Illustrative examples would be those salts formed by reacting the compounds of formula I with hydrochloric, hydrobromic, sulfuric, nitric, phosphoric, phosphorous, maleic, ascorbic, citric, tartaric, pamoic, lauric, stearic, palmitic, oleic, myristic, lauryl-sulfonic, naphthalenesulfonic, linoleic or linolenic acid.

For the purpose of this disclosure, the term "(lower)alkyl" is defined as a straight or branched chain alkyl group having from one to six carbon atoms, e.g. methyl, ethyl, n-propyl, isopropyl, n-butyl, isobutyl, sec-butyl, t-butyl, n-pentyl, isopentyl, 2-methylbutyl, n-hexyl, 2-methylpentyl, 3-methylpentyl, isohexyl, and like groups. The term "cyclo(lower)alkyl" is defined as an alicyclic group having from three to seven carbon atoms, i.e. cyclopropyl, cyclobutyl, cyclopentyl, cyclohexyl and cycloheptyl.

A preferred embodiment of the present invention comprises the compounds of formula I wherein R is —$COR_1$ in which $R_1$ is (lower)alkyl, cyclo(lower)alkyl, phenyl, p-aminophenyl, 3,4,5-trimethoxyphenyl or diphenylmethyl, and the pharmaceutically acceptable acid addition salts thereof. Within this group of compounds, the more preferred compounds are those in which $R_1$ is methyl, n-propyl, cyclopropyl, phenyl, p-aminophenyl, 3,4,5,-trimethoxyphenyl or diphenylmethyl. The most preferred compounds within this group are those in which $R_1$ is p-aminophenyl or diphenylmethyl.

Another preferred embodiment of the present invention comprises the compound of formula I wherein R is —$CONHR_2$ in which $R_2$ is phenyl, and the pharmaceutically acceptable acid addition salts thereof.

Another preferred embodiment of the present invention comprises the compounds of formula I wherein R is —$(CH_2)_3NHCOR_3$ in which $R_3$ is phenyl or diphenylmethyl, and the pharmaceutically acceptable acid addition salts thereof.

The compounds of the present invention may be prepared from the known starting material, 1,3,3-trimethyl-2-azabicyclo[2.2.2]octan-5-endo-ol, by several procedures, depending on the nature of the "R" substituent.

To prepare those compounds of formula I wherein R is —$COR_1$ in which $R_1$ is (lower)alkyl, cyclo(lower)alkyl, phenyl, p-aminophenyl, 3,4,5-trimethoxyphenyl or diphenylmethyl, the alcohol starting material having the formula

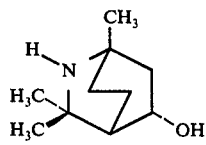

is N-methylated as by treatment with formaldehyde and formic acid to give the intermediate having the formula

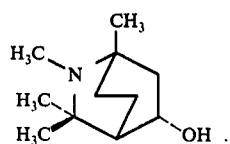

Intermediate III is then esterified in an inert organic solvent to form the desired product I.

The methylation step is preferably carried out by the Eschweiler-Clarke reaction (i.e. with formaldehyde and formic acid) which is a well-known process for the N-methylation of secondary amines such as intermediate II. This step is preferably carried out at elevated temperatures, e.g. 95°–100° C.

The desired esters of formula I may then be prepared by esterification of alcohol intermediate III with an esterifying agent capable of introducing the appropriate ester moiety. Since alcohol III is sterically hindered, the esterifying procedure selected should be one useful for hindered alcohols. A preferred procedure disclosed by G. P. Crowther, et al. in *Org. Synth.* 51:96 (1971) involves reaction of a lithium alkoxide derivative of intermediate III with an acyl halide of the formula

    IV wherein $R_1$ is (lower)alkyl, cyclo(lower)alkyl, phenyl, p-nitrophenyl, 3,4,5-trimethoxyphenyl or diphenylmethyl and X is chloro, bromo or iodo (but preferably chloro). In this procedure, intermediate III is first reacted with an excess of a lithium alkyl, e.g. lithium methyl or lithium n-butyl, in an inert organic solvent such as diethyl ether or tetrahydrofuran. The resulting lithium alkoxide of intermediate III is then reacted in situ with an approximately equivalent amount of acyl halide IV. When the above-described preferred esterification procedure is employed, the reaction is conveniently carried out at room temperature. The compound of formula I where $R_1$ is p-aminophenyl can be prepared from the corresponding p-nitrophenyl product as by catalytic hydrogenation (see Example 2F).

Compounds of formula I wherein R is —(CH$_2$)$_3$NHCOR$_3$ in which R$_3$ is phenyl or diphenylmethyl may be prepared by the process comprising the steps of (a) reacting alcohol III with acrylonitrile in the presence of a base, preferably an alkali metal alkoxide such as sodium t-butoxide, to produce the intermediate having the formula

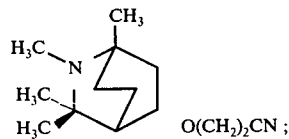    V (b) reducing the nitrile group of intermediate V as by catalytic hydrogenation or treatment with a metal hydride such as AlH$_3$ or LiAlH$_4$ to produce the intermediate having the formula

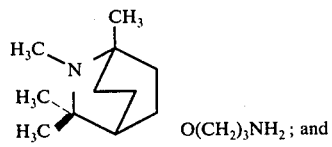    VI (c) acylating the amino group of intermediate VI in an inert organic solvent with an acylating agent of the formula

    VII wherein $R_3$ is phenyl or diphenylmethyl and X is chloro, bromo or iodo (but preferably chloro), or its functional equivalent as an acylating agent for a primary amine, to give the desired product of formula I.

Conversion of alcohol starting material III to the nitrile intermediate V is carried out via the well-known cyanoethylation reaction. The preferred base catalysts for the reaction are alkali metal alkoxides such as sodium methoxide, sodium ethoxide or sodium t-butoxide. Best results are obtained when external heating (e.g. 80°–90° C.) is employed.

Nitrile intermediate V is then reduced to the amine intermediate VI by known procedures. Thus, there may be used catalytic hydrogenation as with a Pd/C catalyst or, alternatively, a chemical reducing agent known to reduce nitrile functional groups to amino groups such as a metal hydride (e.g. LiAlH$_4$ or AlH$_3$). The reduction is conveniently carried out in an inert organic solvent such as diethyl ether or tetrahydrofuran.

The desired products of formula I may then be prepared from intermediate VI by acylation in an inert organic solvent with an acid halide or functional equivalent thereof capable of forming the amide moiety

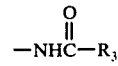

where R$_3$ is phenyl or diphenylmethyl. The preferred procedure involves acylation of intermediate VI with an acid halide of formula VII, preferably the acid chloride, in the presence of an acid acceptor such as a tertiary amine (e.g. triethylamine). Suitable inert organic solvents include aprotic solvents such as benzene, toluene, xylene, methylene chloride, chloroform or dioxane. The acylation may be conducted over a wide temperature range, e.g. from 0°–100° C., but is conveniently carried out at reflux temperature.

For the purpose of this disclosure, the term "functional equivalent" as used in reference to step (c) above is meant to include all those agents commonly known in the art to be useful for the acylation of primary amines, for example, acid anhydrides and mixed acid anhydrides.

The compound of formula I wherein R is —CONHR$_2$ in which R$_2$ is phenyl may be prepared by reacting approximately equimolar amounts of alcohol III and phenyl isocyanate in an inert organic solvent. Suitable solvents are inert aprotic solvents such as benzene, toluene, xylene, methylene chloride, chloroform or dioxane. Good results have been achieved when compound I and phenyl isocyanate are heated under reflux conditions.

Compounds of formula I may be prepared in the free base form or in the form of a pharmaceutically acceptable acid addition salt thereof, e.g. by treatment of the free base compound in a suitable solvent with a pharmaceutically acceptable acid. Alternatively, the acid addition salts of compound I may be converted to the corresponding free base compounds by neutralization with base.

As indicated above, the compounds of formula I and the pharmaceutically acceptable acid addition salts thereof possess antiarrythmic or antihypertensive activity as determined by the pharmacological screening tests described below.

Antiarrhythmic activity was demonstrated by the classical mouse chloroform test which was carried out essentially as described by J. W. Lawson in *Pharmacol Exp. Therap.* 160:22–30 (1968). The test compounds were administered orally (p.o.) or intraperitoneally (i.p.) to female swiss albino mice weighing 16–24 grams. The arrhythmia induced by the chloroform was monitored by electrocardiogram recording and the normal and abnormal heart beats were tabulated. Results of the test for several compounds of the present invention are shown in the table below and are expressed as the $ED_{50}$ or dose required to protect 50% of the test animals against development of ventricular fibrillation by chloroform.

Mouse Chloroform Test
Antiarrhythmic Agent

| R = | Example No. | $ED_{50}$ (mg./kg.) |
|---|---|---|
| —CO—C₆H₂(OCH₃)₃ (2,4,6-trimethoxyphenyl) | 2C | 50 (i.p.) |
| —COC₆H₅ | 2B | 50 (i.p.) |
| —CO(CH₂)₂CH₃ | 2D | 80 (p.o.) |
| —CONHC₆H₅ | 5 | 44 (p.o.) |
|  | 2F | 6.3 (i.p.) |
|  |  | 25 (p.o.) |
| —CO—C₆H₄—NH₂ |  |  |
| —COCH(C₆H₅)₂ | 2G | 12.5 (i.p.) |
|  |  | 20 (p.o.) |
| —(CH₂)₃NHCOC₆H₅ | 3 | 10 (p.o.) |
| —(CH₂)₃NHCOCH(C₆H₅)₂ | 4 | 10 (p.o.) |

Antihypertensive activity was demonstrated in genetically hypertensive (spontaneously hypertensive) rats of the Okamato strain according to the procedure described in *J. Lab. Clin. Med.* 78:957–962 (1971). Five animals were used for each test dose. Results of the test are expressed in the table below as the MED (minimum effective dose) or dose required to give a minimum of a 20 mm Hg drop in blood pressure from control.

Spontaneously Hypertensive Rat Test
Antihypertensive Agent

| R = | Example No. | *MED (mg./kg.) |
|---|---|---|
| —COCH₃ | 1 | 12.5 |
|  | 2A | 25 |
| —CO—cyclopropyl |  |  |

*compounds dosed orally

Certain of the compounds of formula I also demonstrated local anesthetic activity in addition to antiarrythmic activity when tested by the corneal reflex procedure. In this test a corneal reflex was elicited in rabbits by lightly touching the cornea with a stiff hair or bristle which normally would cause the rabbit to blink. The assay was carried out using initially a 2% solution or suspension of the test compound in isotonic saline. A cup or pouch was formed of the lower eyelid by pulling down the lower lid, and one drop of the test compound was instilled into the conjunctival sac of one eye. The other eye serves as a control. The corneal reflex was tested every fifteen minutes until the reflex returned to normal. If the reflex could be elicited 3 out of 5 times, then there was considered to be no local anesthetic effect. If the reflex was blocked and the compound was determined to be a local anesthetic, lower concentrations were tested to determine the minimum concentration needed for local anesthetic activity. Results for several of the compounds of the present invention are expressed in the table below as the MEC (minimum effective concentration) or minimum concentration of compound required for local anesthetic activity.

Local Anesthetic Test
Local Anesthetic Agent

| R = | Example No. | MEC (%) |
|---|---|---|
| —CO—C₆H₄—NH₂ | 2F | 2.0 |
| —COCH(C₆H₅)₂ | 2G | 0.25 |
| —(CH₂)₃NHCOC₆H₅ | 3 | 0.5 |
| —(CH₂)₃NHCOCH(C₆H₅)₂ | 4 | 0.5 |

Those compounds of the present invention possessing antihypertensive activity are useful in the treatment of hypertensive mammals when administered orally in dosages of from about 10–50 mg./kg. Those compounds exhibiting antiarrhythmic activity are useful in the treatment of cardiac arrhythmia in mammals when administering orally or parenterally in doses of from about 10–100 mg./kg. It will be understood that the precise dosage regimen required to treat a subject in need of treatment will depend upon the particular conditions surrounding a specific case, such as the subject being treated, the route and frequency of administration, the extent of treatment required, and the like. These considerations will be determined by the person skilled in the art whose is recommending the treatment in each specific case.

Although the compounds of the present invention can be administered on pure undiluted form, it is advisable to administer them in the form of a pharmaceutical composition with a suitable pharmaceutical vehicle, carrier or diluent.

The following examples are presented to illustrate preparation of the compounds of the present invention.

EXAMPLE 1

Preparation of
5-endo-Acetoxy-1,2,3,3-tetramethyl-2-azabicyclo[2.2.2]octane

A.
1,2,3,3-Tetramethyl-2-azabicyclo[2.2.2]octan-5-endo-ol (intermediate III)

A solution of 1,3,3-trimethyl-2-azabicyclo[2.2.2]octan-5-endo-ol (3.38 g.; 0.02 mole) in 90% formic acid (5.10 g.; 0.10 mole) was prepared by slowly adding the alcohol to the formic acid with cooling. Aqueous formaldehyde (37%; 2.3 ml.) was then added and the solution was heated cautiously at 95°–100° C. for 8 hours. After cooling, 4N HCl (10 ml.) was added, and the solution was evaporated to dryness under reduced pressure, the residue was dissolved in water and the solution was made alkaline with 50% NaOH solution and extracted thoroughly with diethyl ether. The dried (MgSO$_4$) extracts gave a white solid (3.40 g.; 93%), m.p. 101° C. from petroleum ether (b.p. 40°–70° C.).

Anal. Calc'd for C$_{11}$H$_{21}$NO: C, 72.08; H, 11.55; N, 7.64. Found: C, 71.84; H, 11.31; N, 7.65. IR (CHCl$_3$)$\nu_{max}$cm$^{-1}$: 3590, 3400, 2780.

NMR (CCl$_4$): δ0.92 (s, CH$_3$), 1.06 (s, CH$_3$), 1.24 (s, CH$_3$), 2.16 (s, NCH$_3$), 2.56 (s, OH; disappears with D$_2$O), 3.95 (m, CHOH).

B.
5-endo-Acetoxy-1,2,3,3-tetramethyl-2-azabicyclo[2.2.2]-octane (GN-643)

To a solution of 1,2,3,3-tetramethyl-2-azabicyclo[2,2,2]-octan-5-endo-ol (1.83 g.; 0.01 mole) in anhydrous diethyl ether (30 ml.) placed in a three-necked flask fitted with a rubber cap, condenser and dropping funnel, there was slowly added under nitrogen from a syringe a 20–25% solution of n-butyllithium in hexane (3.5 ml.). After stirring for 15 minutes, keeping the temperature near 15° C., there was added dropwise acetyl chloride (0.01 mole) in anhydrous diethyl ether (10 ml.). The resulting slurry was stirred overnight at room temperature, treated with water and extracted thoroughly with diethyl ether. The ether extracts were washed with 5% Na$_2$CO$_3$ and with saturated NaCl solution and dried over MgSO$_4$. After removal of the solvent, the residue was recrystallized (or alternatively distilled in vacuo) to give the title product in 56% yield (b.p. 90°–95° C./0.3 mm Hg), (m.p. 92°–93° C.).

Anal. Calc'd. for C$_{13}$H$_{23}$NO$_2$: C, 69.29; H, 10.29; N, 6.22. Found: C, 69.04; H, 10.47; N, 6.34.

IR (neat)$\nu_{max}$cm$^{-1}$: 2770, 1730.

NMR (CDCl$_3$): δ1.00 (s,CH$_3$), 1.12 (s, CH$_3$), 1.23 (s, CH$_3$), 1.32–2.00 (m, CH + 3CH$_2$), 2.05 (s, COCH$_3$), 2.23 (s, NCH$_3$), 4.96 (m, CHO—)

EXAMPLE 2

The procedure of Example 1 was repeated with the acetyl chloride used therein replaced by an equimolar amount of the acid chlorides indicated in Table A below. There were produced the end-products listed in Table B.

Table A - Acid Chloride

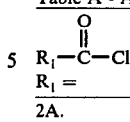

| | R$_1$ = | Table B - End-Product |
|---|---|---|
| 2A. |  | 5-endo-Cyclopropylcarbonyloxy-1,2,3,3-tetramethyl-2-azabicyclo-[2.2.2]octane (GN-644)<br>Yield: 64%<br>B.p.: 113–118° C./0.6 mm Hg.<br>M.p.: 106° C.<br>IR (neat)$\nu_{max}$cm$^{-1}$: 2765, 1720<br>Anal. Calc'd. for C$_{15}$H$_{25}$NO$_2$:<br>  C, 71.67; H, 10.02; N, 5.57.<br>Found: C, 71.57; H, 10.02; N, 5.42. |
| 2B. | —C$_6$H$_5$ | 5-endo-Benzoyloxy-1,2,3,3-tetramethyl-2-azabicyclo(2.2.2]-octane (GN-642)<br>Yield: 70%<br>B.p.: 155–160° C./0.5 mm Hg.<br>IR (neat)$\nu_{max}$ cm$^{-1}$: 2765, 1710<br>NMR (CCl$_4$): δ0.98 (s, CH$_3$), 1.12 (s, CH$_3$), 1.30 (s, CH$_3$), 2.21 (s, NCH$_3$), 5.18 (m, CHO—), 7.45 and 8.00 (2m, C$_6$H$_5$)<br>Anal. Calc'd. for C$_{18}$H$_{25}$NO:<br>  C, 75.22; H, 8.77; N, 4.87.<br>Found: C, 75.31; H, 8.51; N, 4.75. |
| 2C. | 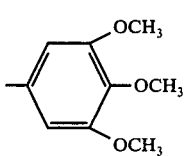 | 5-endo-(3,4,5-Trimethoxybenzoyloxy)-1,2,3,3-tetramethyl-2-azabicyclo[2.2.2]octane (GN-646)<br>Yield: 56%<br>M.p.: 123° C. (recrystallized from anhydrous diethyl ether)<br>IR (CHCl$_3$)$\nu_{max}$cm$^{-1}$: 2780, 1700<br>Anal. Calc'd. for C$_{21}$H$_{31}$NO$_5$:<br>  C, 66.82; H, 8.28; N, 3.71.<br>Found: C, 67.12; H, 7.99; N, 4.01. |
| 2D. | —(CH$_2$)$_2$CH$_3$ | 5-endo-Butyryloxy-1,2,3,3-tetramethyl-2-azabicyclo[2.2.2]-octane (GN-692)<br>Yield: 59%<br>B.p.: 95–100° C./0.5 mm Hg.<br>IR (neat)$\nu_{max}$cm$^{-1}$: 2770, 1730<br>Anal. Calc'd. for C$_{15}$H$_{27}$NO$_2$:<br>  C, 71.10; H, 10.74; N, 5.53.<br>Found: C, 71.11; H, 10.73; N, 5.28. |
| 2E. | —C$_6$H$_4$—NO$_2$(para) | 5-endo-(p-Nitrobenzoyloxy)-1,2,3,3-tetramethyl-2-azabicyclo-[2.2.2]octane<br>Yield: 74%<br>M.p.: 118° C. (recrystallized from petroleum ether, b.p. 40–70° C.)<br>IR (CHCl$_3$)$\nu_{max}$cm$^{-1}$: 2770, 1710<br>Anal. Calc'd for C$_{18}$H$_{24}$N$_2$O$_4$:<br>  C, 65.04; H, 7.28; N, 8.43.<br>Found: C, 65.22; H, 7.36; N, 8.62. |
| 2F. | —C$_6$H$_4$—NH$_2$(para)* | 5-endo-(p-Aminobenzoyloxy)-1,2,3,3-tetramethyl-2-azabicyclo-[2.2.2]octane (GN-645)<br>Yield: 94% (hydrogenation step)<br>M.p.: 129–130° C. (recrystallized from benzene-hexane)<br>IR(CHCl$_3$)$\nu_{max}$cm$^{-1}$: 3470, 3385, 2780, 1685<br>NMR (CCl$_4$): δ0.97 (s, CH$_3$), 1.08 (s, CH$_3$), 1.27 (s, CH$_3$), 1.35–2.10 (m, CH + 3CH$_2$), 2.19 (s, NCH$_3$), 4.08 (s, NH$_2$; disappears with D$_2$O), 5.07 (m, CHO—), 6.51 (d,J = 9, 2H$_{ar}$3,5), 7.73 (d,J = 9, 2H$_{ar}$2,6)<br>Anal. Calc'd for C$_{18}$H$_{26}$N$_2$O$_2$:<br>  C, 71.49; H, 8.67; N, 9.27.<br>Found: C, 71.60; H, 8.73; N, 9.49. |
| 2G. | —CH(C$_6$H$_5$)$_2$ | 5-endo-(Diphenylacetoxy)-1,2,3,3-tetramethyl-2-azabicyclo[2.2.2]-octane (GN-653)<br>Yield: 62%<br>B.p.: 190–195° C./0.1 mm Hg<br>IR (neat)$\nu_{max}$cm$^{-1}$: 2770, 1725<br>NMR (CCl$_3$): δ0,88 (s, CH$_3$), 0.93 (s, CH$_3$), 0.99 (s, CH$_3$), 1.22–2.00 (m, CH + 3CH$_2$), 2.12 (s, NCH$_3$), 4.92 (m, CHO—), 7.28 (near s, C$_6$H$_5$) |

| Table A - Acid Chloride | |
|---|---|
| $R_1 - \overset{\overset{O}{\|}}{C} - Cl$ | |
| $R_1 =$ | Table B - End-Product |
| | Anal. Calc'd for $C_{25}H_{31}NO_2$: |
| | C, 79.54; H, 8.28; N, 3.71. |
| | Found: C, 79.51; H, 8.48; N, 3.81. |

*obtained from the corresponding end-product 2E where R = —$CH_6H_4$—$NO_2$ by catalytic hydrogenation (6 m mole in 25 ml. ethyl acetate, 0.1 g. $PtO_2$ in 25 ml. ethanol, room temperature and atmospheric pressure), followed by chromatography on Florisil ® (dichloromethane, ethyl acetate).
Florisil is the trademark for a magnesium silicate adsorbent sold by Floridin Co., Pittsburgh, Pa.

EXAMPLE 3

Preparation of
5-endo-(3-Benzoylaminoproploxy)-1,2,3,3-tetramethyl-2-azabicyclo[2.2.2]octane (GN-695)

A.

5-endo-(2-Cyanoethoxy)-1,2,3,3-tetramethyl-2-azabicyclo-[2.2.2]octane (intermediate V)

A solution of 7 mg. of sodium in about 1 ml. of t-butyl alcohol was treated with molten 1,2,3,3-tetramethyl-2-azabicyclo-[2.2.2]octan-5-endo-ol (1.83 g.; 0.01 mole). Acrylonitrile (3.34 g.; 0.063 mole) was then added and the solution was heated at 80°-90° C. for 4 hours. Excess acrylonitrile was distilled under reduced pressure, and the resudue was diluted with ethyl acetate and filtered. The filtrate was extracted with 3N HCl, and the acid solution was made alkaline with 10% NaOH solution, saturated with NaCl and extracted thoroughly with diethyl ether. The dried ($MgSO_4$) extracts gave a colorless oil (1.69 g., 72%), b.p. 115°-120° C./0.2 mm Hg, which analyzed as the title product.

IR (neat)$v_{max}$cm$^{-1}$: 2770, 2240

NMR ($CCl_4$): δ0.93 (s, $CH_3$), 1.05 (s, $CH_3$), 1.19 (s, $CH_3$), 2.15 (s, $NCH_3$), 2.50 (t,J = 6, $CH_2CN$), 3.60 (t,J = 6, $OCH_2$), 3.70 (m, CHO—)

Anal. Calc'd for $C_{14}H_{24}N_2O$: C, 71.14; H, 10.23; N, 11.85. Found: C, 71.16; H, 10.08; N, 12.05.

B.

5-endo-(3-Aminopropyloxy)-1,2,3,3-tetramethyl-2-azabicyclo-[2.2.2]octane (intermediate VI)

A solution of 5-endo-(2-cyanoethoxy)-1,2,3,3-tetramethyl-2-azabicyclo[2.2.2]octane (6.0 g.; 0.025 mole) in anhydrous diethyl ether (50 ml.) was added dropwise with stirring and cooling to a solution of $LiAlH_4$ (1.9 g.; 0.05 mole) in anhydrous diethyl ether (50 ml.). The reaction mixture was stirred overnight at room temperature and treated dropwise with water (2 ml.), 15% NaOH solution (2 ml.) and finally water (4 ml.) with continued cooling and stirring. The ether solution was decanted from the granular residue, the residue was washed thoroughly with diethyl ether and the washings and solution were combined and dried ($MgSO_4$). Removal of the solvent and distillation in vacuo gave a colorless oil (5.05 g.; 84%), b.p. 110°-115° C./0.6 mm Hg, which analyzed as the title product.

IR (neat)$v_{max}$cm$^{-1}$: 3350, 3270, 2770, 1580

NMR ($CCl_4$): δ0.93 (s, $CH_3$), 1.04 (s, $CH_3$), 1.18 (s, $CH_3$), 1.2-2 (m, $4CH_2$ + CH + $NH_2$), 2.15 (s, $NCH_3$), 2.75 (t,J = 6.6, $CH_2N$), 3.44 (near t,J = 6.6, $OCH_2$), 3.70 (m, CHO—).

Anal. Calc'd for $C_{14}H_{28}N_2O$: C, 69.95; H, 11.74; N, 11.65. Found: C, 70.17; H, 11.78; N, 11.37.

C.

5-endo-(3-Benzoylaminopyloxy)-1,2,3,3-tetramethyl-2-azabicyclo[2.2.2]octane

Benzoyl chloride (0.01 mole) in anhydrous benzene (10 ml.) was added dropwise with stirring and ice-cooling to a solution of 5-endo-(3-aminopropyloxy)-1,2,3,3-tetramethyl-2-azabicyclo-[2.2.2]octane (2.4 g.; 0.01 mole) and anhydrous triethylamine (1.11 g.; 0.011 mole) in anhydrous benzene (40 ml.). The reaction mixture was refluxed for 1 hour, cooled and filtered. The residue was washed thoroughly with hot benzene and ethyl acetate and the filtrate and washings were combined, washed with 5% NaOH solution, saturated NaCl solution and water, and dried ($MgSO_4$). After removal of the solvents under reduced pressure, the residue was chromatographed on Florisil ® (ether solvent) and distilled in vacuo (alternatively, the product may be recovered by recrystallization from a suitable solvent). The title product was recovered in 48% yield; b.p. 195°-200° C./0.6 mm Hg; m.p. 71°-72° C. (recrystallized from petroleum ether (b.p. 40°-70° C.). IR (neat)-$\mu_{max}$cm$^{-1}$: 3300, 3050, 2770, 1635, 1525. NMR ($CCl_4$): δ0.92 (s, $CH_3$), 1.03 (s, $CH_3$), 1.17 (s, $CH_3$), 1.4-2.0 (m, CH + $4CH_2$), 2.15 (s, $NCH_3$), 3.2-3.9 (m, $OCH_2$ + $NCH_2$), 7.2-7.6 (m, NH + $3H_{ar}$), 7.7-8.0 (m, $2H_{ar}$).

Anal. Calc'd for $C_{21}H_{32}N_2O_2$: C, 73.22; H, 9.36; N, 8.13. Found: C, 73.04; H, 9.66; N, 8.05.

EXAMPLE 4

Preparation of
5-endo-(3-Diphenylacetylaminopropyloxy)-1,2,3,3-tetramethyl-2-azabicyclo[2.2.2]octane (GN-702)

The procedure of Example 3 was repeated with the benzoyl chloride used therein replaced by an equimolar amount of diphenylacetyl chloride. There was produced the title product in 67% yield; m.p. 114° C. (recrystallized from anhydrous diethyl ether). IR (KBr)$v_{max}$cm$^{-1}$: 3265, 3070, 2770, 1640, 1545.

Anal. Calc'd for $C_{28}H_{38}N_2O_2$: C, 77.38; H, 8.81; N, 6.45. Found: C, 77.49; H, 9.07; N, 6.27.

EXAMPLE 5

Preparation of
5-endo-Phenylcarbamoyloxy-1,2,3,3-tetramethyl-2-azabicyclo[2.2.2]octane (GN-729)

A solution of 1,2,3,3-tetramethyl-2-azabicyclo[2.2.-2]octan-5-endo-ol (3.66 g.; 0.02 mole) and phenyl isocyanate (0.02 mole) in anhydrous benzene (30 ml.) was refluxed for 6 hours. The cooled solution was extracted with 2N HCl and the acid extracts were made alkaline with 5% NaOH solution, saturated with NaCl and extracted thoroughly with diethyl ether. The dried ($MgSO_4$) extracts gave a colorless oil by distillation in vacuo (3.85 g., 64%) which analyzed as the title product; b.p. 185°-190° C./0.5 mm Hg. IR (neat)$v_{max}$cm$^{-1}$: 3310, 2775, 1698. NMR ($CCl_4$): δ0.93 (s, $CH_3$), 1.05 (s, $CH_3$), 1.19 (s, $CH_3$), 2.17 (s, $NCH_3$), 4.95 (m, CHO—), 7.00 (m, NH), 7.05 and 7.45 (2m, $C_6H_5$).

Anal. Calc'd for $C_{18}H_{26}N_2O_2$: C, 71.49; H, 8.66; N, 9.26. Found: C, 71.43; H, 8.70; N, 9.16.

We claim:

1. A compound having the formula

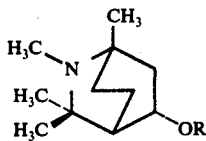

wherein R is —COR₁ in which R₁ is cyclo(lower)alkyl, p-aminophenyl, 3,4,5-trimethoxyphenyl or diphenylmethyl, —CONHR₂ in which R₂ is phenyl, or —(CH₂)₃NHCOR₃ in which R₃ is phenyl or diphenylmethyl; or a pharmaceutically acceptable acid addition salt thereof.

2. A compound having the formula

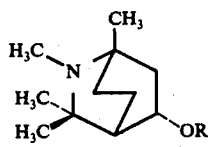

wherein R is —COR₁ in which R₁ is cyclo(lower)alkyl, p-aminophenyl, 3,4,5-trimethoxyphenyl or diphenylmethyl, or a pharmaceutically acceptable acid addition salt thereof.

3. A compound of claim 2 wherein R₁ is p-aminophenyl or diphenylmethyl, or a pharmaceutically acceptable acid addition salt thereof.

4. The compound of claim 2 wherein R₁ is p-aminophenyl, or a pharmaceutically acceptable acid addition salt thereof.

5. The compound of claim 2 wherein R₁ is 3,4,5-trimethoxyphenyl, or a pharmaceutically acceptable acid addition salt thereof.

6. The compound of claim 2 wherein R₁ is diphenylmethyl, or a pharmaceutically acceptable acid addition salt thereof.

7. The compound having the formula

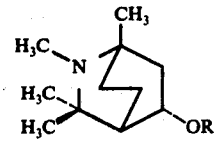

wherein R is —CONHR₂ in which R₂ is phenyl, or a pharmaceutically acceptable acid addition salt thereof.

8. A compound having the formula

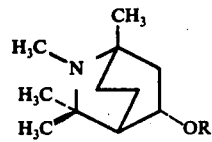

wherein R is —(CH₂)₃NHCOR₃ in which R₃ is phenyl or diphenylmethyl, or a pharmaceutically acceptable acid addition salt thereof.

9. The compound of claim 8 wherein R₃ is phenyl, or a pharmaceutically acceptable acid addition salt thereof.

10. The compound of claim 8 wherein R₃ is diphenylmethyl, or a pharmaceutically acceptable acid addition salt thereof.